United States Patent
Panicali et al.

(12) 
(10) Patent No.: US 6,319,496 B1
(45) Date of Patent: *Nov. 20, 2001

(54) GENERATION OF HUMAN CYTOTOXIC T-CELLS SPECIFIC FOR CARCINOMA SELF-ASSOCIATED ANTIGENS AND USES THEREOF

(75) Inventors: Dennis L. Panicali, Acton, MA (US); Jeffrey Schlom, Potomac, MD (US)

(73) Assignees: Therion Biologics Corporation, Cambridge, MA (US); The United States of America as represented by the Department of Health & Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/287,221

(22) Filed: Apr. 6, 1999

Related U.S. Application Data

(63) Continuation of application No. 08/396,385, filed on Feb. 22, 1995, now Pat. No. 6,001,349.

(51) Int. Cl.[7] .......................... A61K 48/00; C12N 15/00; C12N 15/88
(52) U.S. Cl. .................................... 424/93.21; 424/93.21; 435/69.1; 435/370.1; 435/455; 435/325; 514/2; 514/44
(58) Field of Search .................................. 424/93.2, 93.21; 435/69.1, 320.1, 455, 325; 514/2, 44

(56) References Cited

U.S. PATENT DOCUMENTS 5,833,975  * 11/1998  Paoletti et al. ................... 424/93.2

FOREIGN PATENT DOCUMENTS

| 0 263 933 | 4/1987 | (EP) . |
| 0 343 946 | 11/1989 | (EP) . |
| WO 96/14074 | 5/1996 | (EP) . |
| WO 92/19266 | 11/1992 | (WO) . |

OTHER PUBLICATIONS

Ngo et al., in The Protein Folding Problem and Tertiary Structure Prediction, 1994, Merz et al., (ed.), Birkhauser, Boston, MA, pp. 433 and 492–495, 1994.*
Schlom, et al., *AIDS Res. Hum. Retrivuryses*, vol. 10:S1, p. S58 Abstract, 1994.
Salgaller, et al., *Cancer Research*, vol. 53, pp. 2154–2161 (1993).
Falk, et al., *Nature* vol. 351, pp. 290–296 (1991).
Schlom, et al., *Breast Cancer Research and Treatment*, vol. 38, No. 1:27–39 (1996).
Tsang, et al., *J. of Nat'l Cancer Inst.*, vol. 87, No.13:982–990 (1995).
Tsang, et al., *Proc. of the Amer. for Can. Res.*, vol. 36, p. 249 (Abstract#1483 (1995).
Mitchel, *J. of Nat'l Cancer Inst.*, vol. 87, No. 13: 949–951 (1995).
Kent, et al., *AIDS Res. Hum. Retroviruses*, vol. 10, No. 5:51–60.
Tannock, et al., *The basic Science of Oncology*, McGraw–Hill, Inc. 1992:238–248.
Mastrangelo, et al., *Seminars in Oncology*, 1996, vol. 23, No. 1:4–21.
Hwu, PPO Updates, 1995, vol. 9, No. 4:1–13.
Bei, et al., *J. Immuno.*, 1994, 16:275–282.
Oesterling, J. E., *J. Urol.* 145:907–923, (1991).
Peace, D. J., et al. *Cancer Vaccine Symposium.* Cancer Research Institute. Oct. 3–5 (1994).
Fisk, B., et al. *Int.J.Oncology* 5:51–63 (1994).
Ioannides, C. G., et al. *J. Immunol*151:3693–3703, (1993).
Jung, S., et al. *J. Exp.Med.* 173: 273–276 (1991).
Fenton, S., et al. *J. Natl.Cancer Inst.* 85: 1294–1302, (1993).
Houblers, J. G. A., et al. *Eur. J. Immunol.* 23: 2072–2077, (1993).
Kantor, J., et al., *J.Natl.Cancer Inst.* 84: 1084–1091, (1992).
Kantor, J., et al. *Cancer Res.* 52: 6925–6927, (1983).
Mavligit, G. M., et al. *Cancer* (Phila) 52: 146–149, (1983).
Collatz, E., et al. *Int.J.Cancer* 8: 298–383, (1971).
Chester, K. A., et al. *Cli.Exp.Immunol.* 58: 685–693 (1984).
Ura, Y., et al. *Cancer Lett.* 24: 283–295, (1985).
Staab, et al. Br. J. Cancer 42:46 (1980).

* cited by examiner

Primary Examiner—Dave T. Nguyen
(74) Attorney, Agent, or Firm—Nixon Peabody LLP

(57) ABSTRACT

We have discovered that by using a recombinant DNA viral vector, preferably a pox virus vector having at least one insertion site containing a DNA segment encoding the carcinoma self-associated antigen, or a cytotoxic T-cell eliciting epitope thereof, operably linked to a promoter capable of expression in the host, human cytotoxic T-cells specific for the carcinoma self-associated antigens can be produced. The method preferably comprises introducing a sufficient amount of the recombinant pox virus vector into a host to stimulate production of cytotoxic T-cells, and contacting the host with additional antigen at periodic intervals thereafter. The additional antigen may be added by using a second pox virus vector from a different pox genus. In another embodiment, additional antigen is added by contacting the host with antigen. The antigen may be formulated with an adjuvant or in a liposomal formulation. The T-cells can be isolated. The number of T-cells can be expanded by contacting the isolated cytotoxic T-cells alternately with the carcinoma self-associated antigen or an epitope thereof and IL-2. The isolated T-cells can be used in a method for treating a host having a tumor expressing a carcinoma self-associated antigen comprising introducing cytotoxic T-cells specific for the antigen to the host and at at least one periodic interval thereafter introducing to the host a T-cell eliciting epitope of the carcinoma self-associated antigen.

16 Claims, 2 Drawing Sheets

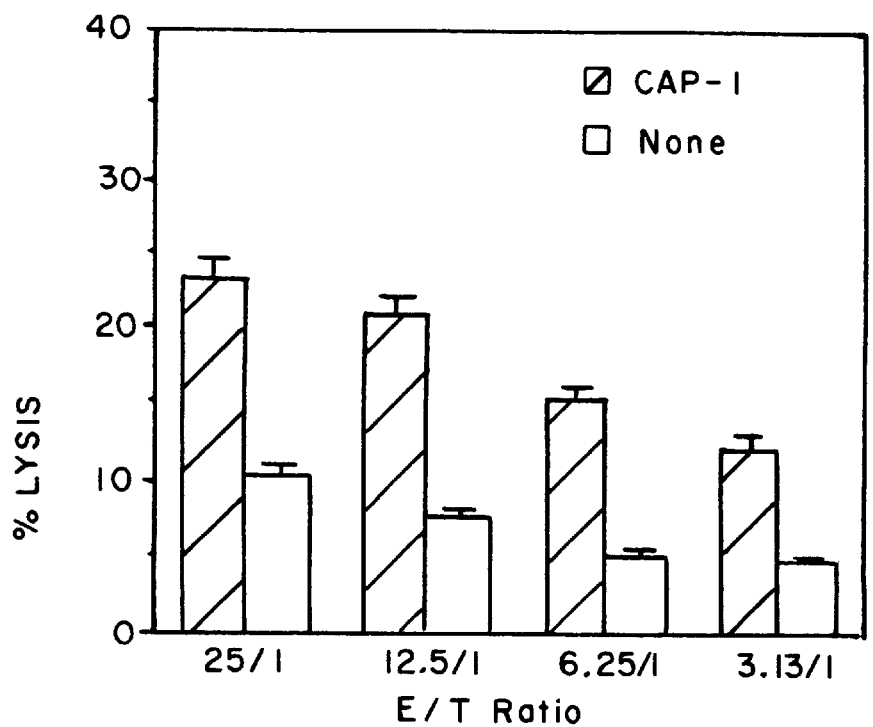
FIG. IA
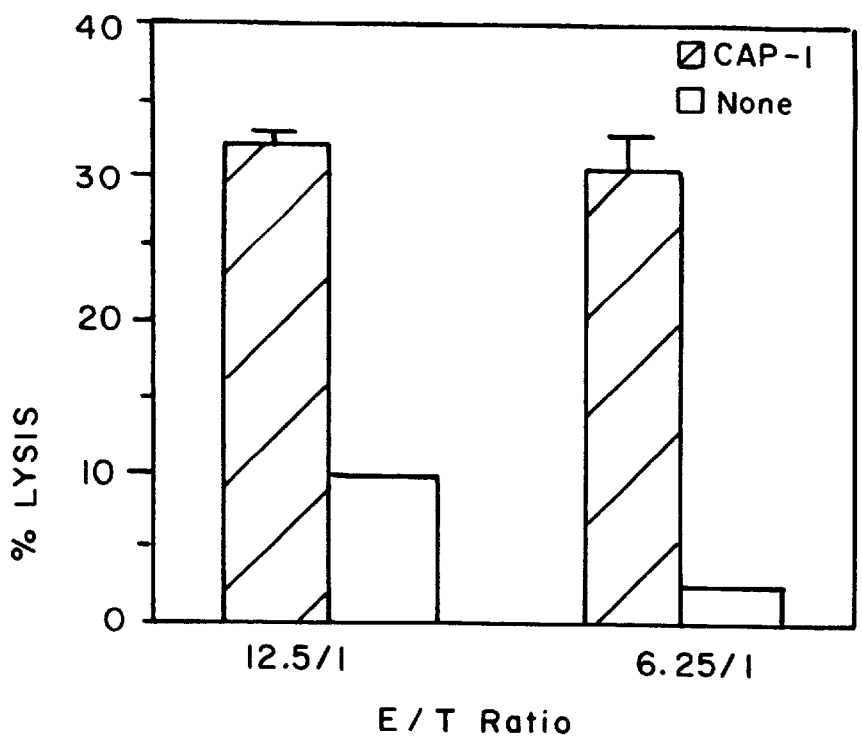
FIG. IB

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:1:

Thr Leu Ser Gly Ala Asn Leu Asn Leu
1               5

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:2:

Val Leu Tyr Gly Pro Asp Thr Pro Ile Ile
1               5                   10

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:3:

Thr Leu His Val Ile Lys Ser Asp Leu Val
1               5                   10

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO:4:

Lys Leu Thr Ile Glu Ser Thr Pro Phe Asn Val
1               5                   10

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:5:

Thr Leu Leu Ser Val Thr Arg Asn Asp Val
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:6:

Leu Leu Val His Asn Leu Pro Gln His Leu
1               5                   10

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:7:

His Leu Phe Gly Tyr Ser Trp Tyr Lys
1               5

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:8:

Thr Leu Phe Asn Val Thr Arg Asn Asp Ala
1               5                   10

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (xi) SEQUENCE DESCRIPTION: SEQ ID NO:9:

Thr Gln Asp Ala Thr Tyr Leu Trp Trp Val
1               5                   10

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:10:

Gly Gln Phe Arg Val Tyr Pro Glu Leu
1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:11:

Tyr Arg Pro Gly Glu Asn Leu Asn Leu
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO:12:

Ala Leu Ala Ala Ala Ala Ala Ala Val
1               5

GENERATION OF HUMAN CYTOTOXIC T-CELLS SPECIFIC FOR CARCINOMA SELF-ASSOCIATED ANTIGENS AND USES THEREOF

This application is a continuation of application Ser. No. 08/396,385, filed on Feb. 22, 1995, now U.S. Pat. No. 6,001,349.

FIELD OF THE INVENTION

The present invention relates generally to generation of human cytotoxic T-cells specific for carcinoma self-associated antigens and uses thereof, for example in epitope mapping and adoptive cell therapy.

BACKGROUND OF THE INVENTION

A number of approaches have been utilized in treating malignant growth of tissue cells in humans such as cancers. While the various approaches identified have frequently been successful in treating a particular cancer, one difficulty has been that there are numerous different cancers. Thus, drugs that treat one type of cancer, often are ineffective against a different type of cancer.

One method that attempts to overcome the difficulties resulting from the differences in cancers is immunotherapy. By such an approach, the immune system can select and create the method of treating a specific cancer. Being able to select and/or identify antigens including specific epitopes that can be used in such an approach is extremely important.

Specific peptides that bind human MHC molecules have now been identified for melanoma associated antigens. Darrow, T. L., et al. *J Immunol* 142: 3329–3335, (1989); Hom, S. S., et al. *J Immunother* 10: 153–164, (1991); Cox, A. L., et al. *Science* 264: 716–719 (1994); Olive, D., et al. *Cancer Vaccine Symposium.* Cancer Research Institue. Oct. 3–4 (1994). MHC class I and/or class II peptide complexes have been reported as being recognized by human T-cells. The ability to activate T-cells by cytokines or co-stimutatory molecules is thus extremely important.

The identification of human carcinoma associated antigens and epitopes that might be recognized by human T-cells is also currently under active investigation. Molecules such as prostate specific antigen (PSA), [Oesterling, J. E., J Urol 145: 907–923, (1991); Peace, D. J., et al *Cancer Vaccine Symposium.* Cancer Research Institute. Oct. 3–5 (1994)], neu/c-erbB2 [Fisk, B., et al. *Int J Oncology* 5: 51–63 (1994)] MUC-1 [loannides, C. G., et al. *J Immunol* 151: 3693–3703, (1993)] point mutated ras [Tsang, K. Y., et al. *Vaccine Research* (in press); Jung, S., et al. *J Exp Med* 173: 273–276 (1991); Fenton, S., et al. *J Natl Cancer Inst* 85: 1294–1302, (1993)] point mutated p53 [Houblers, J. G. A., et al *Eur J Immunol* 23: 2072–2077, (1993)] and carcinoembryonic antigen (CEA) [Kantor, J., et al. *J Natl Cancer Inst* 84: 1084–1091, (1992); Kantor, J., et al *Cancer Res* 52: 6917–6925, (1992); Ras, E., et al. European Immunology meeting, Barcelona, June (1994)] are among such candidates. One difficulty has been that many of these antigens are normal self-antigens, which therefore are not expected to trigger an immune response of the type needed for therapeutic approaches.

For example, while human CEA is extensively expressed on the vast majority of human colorectal, gastric and pancreatic carcinomas as well as approximately 50% of breast cancers and 70% of non-small cell lung cancers [Thompson, J. A., et al. *J Clin Lab Anal* 5: 344–366, (1991)], CEA is also expressed at least to some extent on normal colon epithelium and in some fetal tissue. The CEA gene has been sequenced and shown to be part of the human immunoglobulin gene superfamily, and thus shares some homology with other molecules found on normal human tissues. Thompson, J. A., et al. *J Clin Lab Anal* 5: 344–366, (1991); Oikawa, S., et al. *Biochem Biophys Res Commun* 144: 634–642, (1987). At the amino acid level, CEA shares approximately 70% homology with NCA (non-specific cross reacting antigen) which is found on normal granulocytes. Thompson, J. A., et al. supra.

However, the immunogenicity of CEA in normal humans or cancer patients is at best suspect. Although several papers claim antibodies to CEA in patients, [Staab, H. J., et al *Br J Cancer* 42: 26–33, (1980); Mavligit, G. M., et al. *Cancer* (Phila) 52: 146–149, (1983)] others claim these observations are artifacts [Collatz, E., et al *Int J Cancer* 8: 298–303, (1971); Chester, K. A., et al *Clin Exp Immunol* 58: 685–693, (1984); Ura, Y., et al. *Cancer Lett* 24: 283–295, (1985)]. No reports of the presence or absence of T-cell responses to CEA exist.

There are two types of immune response—antigen specific responses producing antibodies, and cell specific responses eliciting cytotoxic T-cells.

Improved methods for eliciting an immune response to self-antigen would be extremely useful.

For example, cytotoxic T-cells elicited by a self-antigen can be used in somatic cell therapy, in identifying epitopes and small peptides that induce a cytoxic T-cell response and in drug assays for compounds that enhance a specific cytoxic T-cell response.

The availability of human cytotoxic T-cells specific for carcinoma self-associated antigens also allow for mapping of the epitopes recognized by the T-cells. These epitopes can in turn be used to prime or boost the immune-system to expand the T-cell population either in vivo or in vitro. The in vitro cells as aforesaid can then be transferred back into a patient as is currently done in TIL cell therapy and used to treat a tumor expressing the antigen.

SUMMARY OF THE INVENTION

We have discovered that by using a recombinant DNA viral vector, preferably a pox virus vector having at least one insertion site containing a DNA segment encoding the carcinoma self-associated antigen, or a cytotoxic T-cell eliciting epitope thereof, operably linked to a promoter capable of expression in the host, human cytotoxic T-cells specific for the carcinoma self-associated antigens can be produced. The method preferably comprises introducing a sufficient amount of the recombinant pox virus vector into a host to stimulate production of cytotoxic T-cells, and contacting the host with additional antigen at periodic intervals thereafter. The additional antigen may be added by using a second pox virus vector from a different pox genus. In another embodiment, additional antigen is added by contacting the host with antigen. The antigen may be formulated with an adjuvant or in a liposomal formulation.

We have also discovered that human cytotoxic T-cells specific for carcinoma self-associated antigens can be produced using a cytotoxic T-cell eliciting epitope of the carcinoma self-associated antigen. The method preferably comprises introducing the T-cell eliciting epitope into a host to stimulate production of cytotoxic T-cells. If necessary, in order to boost production of the cytotoxic T-cells, at periodic intervals thereafter, the host is contacted with additional T-cell eliciting epitope. The epitope may be formulated with adjuvant or may be in a liposomal formulation. Alternatively, additional T-cell elicting epitope may be added using a pox virus vector.

Carcinoma self-associated antigens include, for example, carcinoembryonic antigen (CEA), prostate specific antigen (PSA), TAG-72, IL-2r and neulc-erbB-2. CEA is preferred.

Cytotoxic T-cell eliciting epitopes of the carcinoma self-associated antigens may also be used. For CEA, preferred epitopes comprise peptides represented in the Sequence Listing as SEQ ID NO:1, 2, 3, 4, 5, 6, 7, 8, 9 and 10.

The pox virus is preferably selected from the group of pox viruses consisting of suipox, avipox, capripox and orthopox virus. Preferred orthopox include vaccinia, rabbitpox and racoon pox. Preferred avipox includes fowlpox, canary pox and pigeon pox. A more preferred avipox is fowlpox. The preferred suipox is swinepox.

Vaccinia viral vectors may elicit a strong antibody response, thus while numerous boosts with vaccinia vectors are possible, its repeated use is not preferred. We have discovered that by using pox from different genera to boost, this sensitivity problem can be minimized. In accordance with the present invention, in order to avoid such problems, preferably, when the first or initial pox virus vector is vaccinia, the second and subsequent pox virus vectors are selected from the pox viruses from a different genus such as suipox, avipox, capripox other than vaccinia.

Adjuvants include, for example, RIBI Detox, Q521, and incomplete Freund's adjuvant. Liposomal formulations can also be used.

Human cytotoxic T-cells specific for a carcinoma self-associated antigens produced in accordance with the present invention can be isolated from a human host. These cells can be used in drug assays, used to map cytotoxic T-cell eliciting antigen epitopes or in adoptive cell therapy.

BRIEF DESCRIPTION OF THE DRAWINGS

FIG. 1A and FIG. 1B show cytotoxicity of a T-cell lines [designated V24T (FIG. 1A) and V6T (FIG. 1B)] derived from patients immunized with rV-CEA; and induced by CEA CAP-1 peptide. CTL activity was determined in a 18 hr $^{111}$In-release assay using T2 cells as target incubated with CAP-1 peptide (50 µg/ml).

DETAILED DESCRIPTION OF THE INVENTION

Figure 2:
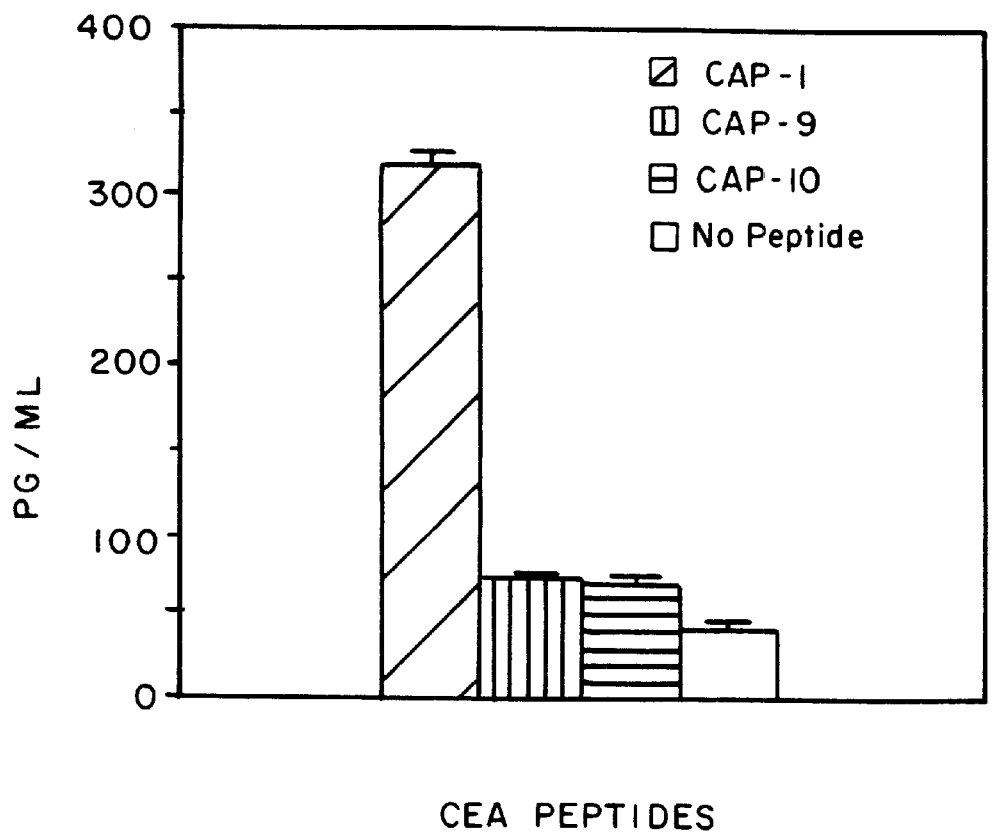
FIG. 2 depicts secretion of TNF-alpha by T-VAC24 cell line in response to stimulation of autologous B-cells pulsed with CEA peptide. The supernant was screened for TNF-alpha secretion using a ELSIA during a 3 day incubation of V24T-cells with autologous B cells and CEA peptide (50 µg/ml).

We have induced T-cell immunity to CEA in carcinoma patients by placing the CEA gene into a recombinant viral vector, i.e, a pox vector such as vaccinia virus. Vaccinia is a preferred vector for several reasons. Among these are: (a) its wide use in humans in the eradication of smallpox; (b) its ability to infect a wide range of cells, including professional antigen presenting cells, and express the inserted gene product in a manner that it has the potential to be processed in the context of class I and/or class II MHC molecules; and (c) animal model studies have shown that the use of a recombinant human CEA vaccinia virus (designated rV-CEA) is superior to the use of soluble CEA in the induction of anti-tumor effects on established CEA expressing tumors. Kantor, J., et al. *J Natl Cancer Inst* 84: 1084–1091, (1992). These findings correlated with the appearance of CEA specific CTLs in rV-CEA inoculated animals. Kantor, J., et al., supra.

Animal model studies demonstrate that rV-CEA can indeed infect mammalian cells in vivo to a level as to induce immune responses and demonstrate lack of toxicity.

rV-CEA has also been administered to rhesus monkeys and has been shown to induce CEA-specific T-cell responses with no toxicity. Kantor, J., et al *Cancer Res* 52: 6917–6925, (1992).

Cytotoxic T-cell lines can also be generated using a cytotoxic T-cell eliciting epitope of a carcinoma self-associated antigen.

As used herein a carcinoma self-associated antigen refers to an antigen that is native to the animal and associated with malignant tumors. Preferred self-associated antigens include, for example, CEA, PSA, neu/c-erbB-2, TAG-72 and IL-2r. More, preferably, the antigens are CEA and PSA. Even more preferably CEA.

Viral Vector

Basic techniques for preparing recombinant DNA viruses containing a heterologous DNA sequence encoding the carcinoma self-associated antigen or cytotoxic T-cell eliciting epitope are known to the skilled artisan and involve, for example, homologous recombination between the viral DNA sequences flanking the DNA sequence in a donor plasmid and homologous sequences present in the parental virus (Mackett, et al., *Proc. Natl. Acad. Sci. USA* 79:7415–7419 (1982)). For example, recombinant viral vectors such as a pox viral vector can be used in delivering the gene. The vector can be constructed for example by steps known in the art, e.g. analogous to the methods for creating synthetic recombinants of the fowlpox virus described in U.S. Pat. No. 5,093,258, the disclosure of which is incorporated herein by reference. Other techniques include using a unique restriction endonuclease site that is-naturally present or artificially inserted in the parental viral vector to insert the heterologous DNA.

Pox viruses useful in practicing the present invention include orthopox, suipox, avipox and capripoxvirus.

Orthopox include vaccinia and ectomelia, raccoon pox. The preferred orthopox is vaccinia.

Avipox includes fowlpox, canary pox and pigeon pox. The preferred avipox is fowlpox.

A preferred suipox is swinepox.

Other viral vectors that can be used include herpes virus, retroviruses, polio, and adenoviruses.

For example, the DNA gene sequence to be inserted into the virus can be placed into a donor plasmid, e.g., an *E. coli* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. With a parental pox viral vector, a pox promoter is used. The resulting plasmid construct is then amplified by growth within *E. coli* bacteria and isolated. Preferably, the plasmid also contains an origin of replication such as the *E. coil* origin of replication, and a marker such as an antibiotic resistance gene for selection and propagation in *E. coli*.

Second, the isolated plasmid containing the DNA gene sequence to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al., *J. Virology,* 60:920 (1986) (shope fibroma virus); capripoxvirus: Gershon, et al., *J. Gen. Virol.,* 70:525 (1989) (Kenya sheep-1); orthopoxvirus: Weir, et al., *J. Virol.,* 46:530 (1983) (vaccinia); Esposito, et al., *Virology,* 135:561 (1984) (monkeypox and variola virus); Hruby, et al., *PNAS,* 80:3411 (1983) (vaccinia); Kilpatrick, et al., *Virology,* 143:399 (1985) (Yaba monkey tumor virus); avipoxvirus: Binns, et al., *J. Gen. Virol.* 69:1275 (1988) (fowlpox); Boyle, et al., *Virology,* 156:355 (1987) (fowlpox); Schnitzlein, et al., *J. Virological Methods,* 20:341 (1988) (fowlpox, quailpox); entomopox (Lytvyn, et al., *J. Gen. Virol.* 73:3235–3240 (1992))].

In vaccinia, in addition to the TK region, other insertion regions include, for example, HindIII M.

In fowlpox, in addition to the TK region, other insertion regions include, for example, BamHI J [Jenkins, et al., *AIDS Research and Human Retroviruses* 7:991–998 (1991)] the EcoRI-HindIII fragment, BamHI fragment, EcoRV-HindIII fragment, BamHI fragment and the HindIII fragment set forth in EPO Application No. 0 308 220 A1. [Calvert, et al., *J. of Virol.* 67:3069–3076 (1993); Taylor, et al., *Vaccine* 6:497–503 (1988); Spehner, et al., (1990) and Boursnell, et al., *J. of Gen. Virol.* 71:621–628 (1990)].

In swinepox preferred insertion sites include the thymidine kinase gene region.

In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. For example in poxviruses, pox viral promoters should be used, such as the vaccinia 7.5K, 40K or fowlpox promoters such as FPV C1A. Enhancer elements can also be used in combination to increase the level of expression. Furthermore, the use of inducible promoters, which are also well known in the art, in some embodiments are preferred.

Generation Cytotoxic T-Cells

Cytotoxic T-Cells specific for the desired self-associated antigen can be generated by administering between about $10^5$–$10^9$ pfu of the recombinant pox virus, constructed as discussed above to a host. The preferred host is a human. However, a transgenic mammal, e.g., mouse, having a human-like immune system may also be used. At at least one interval thereafter, which is preferably one to three months later, the immune response is boosted by administering additional antigen or a T-cell stimulating epitope thereof to the host. More preferably there is at least a second "boost" preferably one to three months after the first boost. The antigen may preferably be administered using a second pox virus vector from a different pox genera, or may be administered directly using, for example, an adjuvant or liposome. Cytokines, e.g., IL-2, or co-stimulatory molecules, e.g., B7.1, B7.2, may be used as biologic adjuvants and can be administered systemically to the host or co-administered via insertion of the genes encoding the molecules into the recombinant pox vector.

Adjuvants include, for example, RIBI Detox (Ribi Immunochemical), QS21 and incomplete Freund's adjuvant.

Cytotoxic T-cells can be isolated from peripheral blood mononuclear cells (PBMC) obtained from the host. For example, PBMC can be separated by using Lymphocyte Separation Medium gradient (Organon Teknika, Durham, N.C., USA) as previously described [Boyum, et al., *Scand J. Clin Lab Invest* 21: 77–80 (1968)]. Washed PBMC are resuspended in a complete medium, for example, RPMI 1640 (GIBCO) supplemented with 10% pool human AB serum (Pel-Freeze Clinical System, Brown Dear, Wis., USA), 2 mM glutamine, 100 U/ml penicillin and 100 μg/ml of streptomycin (GIBCO). About $2\times10^5$ cells in complete medium in a volume of, for example, 100 μl are added into each well of a 96-well flat-bottom assay plate (Costar, Cambridge, Mass., USA). The antigen or peptides are added into the cultures in a final concentration of about 50 μg/ml and incubated at 37° C. in a humidified atmosphere containing 5% $CO_2$. The cultures are provided with fresh human IL-2 (10 U/ml) after 5 days and replenished with IL-2 containing medium every 3 days. Primary cultures are restimulated with the same peptide (50 μg/ml) on day 16. $5\times10^5$ irradiated (4,000 rad) autologous PBMC are added in a volume of about 50 μl complete medium as antigen-presenting cells (APC). About five days later, the cultures are provided with human mIL-2 containing medium as described previously. Cells are restimulated for 5 days at intervals of 16 days.

Epitope Mapping

The cytotoxic T-cells of the present invention can be used to determine the epitope of the carcinoma associate self-antigen that elicits a cytoxic T-cell. For example, one can cut the antigen (protein) into numerous peptide fragments. Alternatively, the fragments can be chemically synthesized. Cytotoxic T-cells can then be plated and different fragments added to different wells. Only T-cells which recognize one of the pre-selected peptide fragments as an epitope will continue to expand, thereby permitting ready identification.

These fragments can then be used to elicit cytotoxic T-cell instead of using the whole protein. Additionally, one can prepare other fragments containing the epitope to enhance its ability to elicit a cytoxic T-cell response. Modifications to these fragments are well known in the art and include the use of conjugates, specific amino acid residues such as cystines, etc.

Drug Assay

The cytotoxic T-cell can also be used to screen for compounds which enhance the ability of the antigen to create a cytotoxic T-cell response. For example, cytotoxic T-cells can be incubated with a selected epitope, for example, in a microtiter plate. The compound to be tested, e.g. a drug, is then added to the well and the growth of the T-cells is measured. T-cell expansion indicates that the test compound enhances the T-cell response. Such compounds can be further evaluated.

Therapy

The cytotoxic T-cell can be cultured to amplify its number and then injected back into the host by a variety of means. Generally, between $1\times10^5$ and $2\times10^{11}$ cytotoxic T-cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional antigen or fragments containing T-cell eliciting epitope(s) may be administered to the patient to further expand the T-cell number. The antigen or epitope may be formulated with an adjuvant and/or may be in a liposomal formulation.

The cytotoxic T-cells can also be modified by introduction of a viral vector containing a DNA encoding TNF and reintroduced into a host in an effort to enhance the anti-tumor activity of the cells. Other cytokines can also be used.

For parenteral administration, the recombinant vectors or the cytotoxic T-cells will typically be injected in a sterile aqueous or non-aqueous solution, suspension or emulsion in association with a pharmaceutically-acceptable parenteral carrier such as physiological saline.

Reference Example 1

Construction of Vectors

Pox Viruses

A number of pox viruses have been developed as live viral vectors for the expression of heterologous proteins (Cepko et al., Cell 37:1053–1062 (1984); Morin et al., Proc. Natl. Acad. Sci. USA 84:4626–4630 (1987); Lowe et al., Proc. Natl. Acad. Sci. USA, 84:3896–3900 (1987); Panicali & Paoletti, Proc. Natl. Acad. Sci. USA, 79:4927–4931 (1982); Machett et al., Proc. Natl. Acad. Sci. USA, 79:7415–7419 (1982)). Representative fowlpox and swinepox virus are available through the ATCC under accession numbers VR-229 and VR-363, respectively. A recombinant vaccinia—CEA is available through the ATCC under accession number VR2323.

DNA Vectors for in vivo Recombination with a Parent Virus

Genes that code for desired carcinoma associated antigens are inserted into the genome of a pox virus in such a manner as to allow them to be expressed by that virus along with the expression of the normal complement of parent virus proteins. This can be accomplished by first constructing a DNA donor vector for in vivo recombination with a pox virus.

In general, the DNA donor vector contains the following elements:

(i) a prokaryotic origin of replication, so that the vector may be. amplified in a prokaryotic host;

(ii) a gene encoding a marker which allows selection of prokaryotic host cells that contain the vector (e.g., a gene encoding antibiotic resistance);

(iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be monodi-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., J. Virol., 62:1046 (1988); Falkner and Moss., J. Virol., 62:1849 (1988); Franke et al., Mol. Cell. Biol., 5:1918 (1985), as well as genes such as the E. coil lacZ gene, that permit identification of recombinant viral plaques by calorimetric assay (Panicali et al., Gene, 47:193–199 (1986)).

Integration of Foreign DNA Sequences into the Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112, WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK⁻ and can be selected on this basis (Mackett et al., Proc. Natl. Acad. Sci USA, 79:7415 (1982)). Alternatively, co-integration of a gene encoding a marker or indicator gene with the foreign gene(s) of interest, as described above, can be used to identify recombinant progeny. One preferred indicator gene is the E. coli lacZ gene: recombinant viruses expressing β-galactosidase can be selected using a chromogenic substrate for the enzyme (Panicali et al., Gene, 47:193 (1986)).

Following in vivo recombination, recombinant viral progeny can be identified by one of several techniques. The presence of integrated foreign DNA can be detected by hybridization with a labeled DNA probe specific for the inserted DNA. Preferred techniques for selection, however, are based upon co-integration of a gene encoding a marker or indicator gene along with the gene of interest, as described above. A preferred indicator gene is the E. coli lacZ gene which encodes the enzyme β-galactosidase. Selection of recombinant virus expressing β-galactosidase can be done by employing a chromogenic substrate for the enzyme. For example, recombinant viruses are detected as blue plaques in the presence of the substrate 5-bromo-4-chloro-3-indolyl-β-D-galactosidase or other halogenated-indolyl-β-D-galactosidase (e.g., BluGal™).

Characterizing the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA).

EXAMPLE I

Cytotoxic T-cell Response in Mouse Model

Materials and Methods

Cells

The MC-38 murine colonic adenocarcinoma cell line was supplied by the laboratory of Dr. S. Rosenberg (National Cancer Institute, Bethesda, Md.). The derivative cell line expressing human CEA, designated MC-38-CEA-2, was developed by the transduction of the human CEA gene by the retroviral expression vector pBNC and has been previously described. Robbins, PF, et al., Cancer Res 1991; 51:3657–62.

Recombinant Baculovirus CEA (bV-CEA)

Recombinant baculovirus CEA (bV-CEA) has been previously described as BVCEA-140. Salgaller, ML, et al., Cancer Res. 1993;53:2154–61. bV-CEA encodes the full length human CEA gene and expresses several distinct molecular weight species ranging from 140 kDa to 110 kDa. These products reflect the genetic heterogeneity of the recombinant bV-CEA proteins due to homologous recombination between the three repeated domains of CEA. bV-CEA was purified from whole cell extract of the infected *Spodoptera frugiperda* cells as previously described. Salgaller, ML, et al., Cancer Res. 1993;53:2154–61. It has previously been shown that bV-CEA contains at least 10 CEA epitopes by reactivity to different monoclonal antibodies. Bei, R., et al., *Mole Immunolo* 1994;31:771–780. bV-CEA was shown to contain only simple high mannose carbohydrates as well as biantennary and biantennary hybrid carbohydrates, while native CEA also contains triantennary and tetraantennary complex sugars. Bei, R., et al., *Mole Immunolo* 1994; 31:771–780. bV-V has been previously described. Salgaller, ML, et al., *Cancer Res.* 1993;53:2154–61. It is the recombinant baculovirus containing only the shuttle vector with no CEA insert.

Recombinant Vaccinia CEA (rV-CEA)

Recombinant vaccinia CEA was generated as previously described by Kantor, J., et al., *Cancer Res.* 1992;52:6917–25, the disclosure of which is herein incorporated by reference.

Native CEA (nCEA)

Commercially purified human CEA, designated nCEA for native CEA, was purchased from Vitro Diagnostic (Littleton, Colo.). It was derived from a liver adenoma.

Immunization Protocol

Six to eight weeks old female C57BL/6 mice were employed for the different immunization regimens. Animals were immunized either with purified native (nCEA) or recombinant CEA (bV-CEA). In each group of 10 animals, either, human CEA, purified bV-CEA or PBS alone in adjuvant was administered subcutaneously three times, at 14 day intervals. Each animal received 25 $\mu$g of the purified protein for each immunization. The immunogens were emulsified in 25 $\mu$g of monophosphoryl lipid A (MPL)+ synthetic trehalose dicorynomycolate(TDCM)+cell wall skeleton (CWS) adjuvant (RIBI Immunochem Research, Inc., Hamilton, Mont.) in 200 $\mu$l of phosphate buffered saline (PBS) (Biofluids Inc., Rockville, Md.). Other groups of animals were primed with recombinant vaccinia CEA (rV-CEA) followed by immunization with the purified proteins. Ten animals in each group were inoculated by tail scarification with $1\times10^7$ plaque forming units (pfu) of rV-CEA in 10 $\mu$l of PBS. Subsequently the animals were boosted 14 days apart twice with 25 $\mu$g of either nCEA, purified bV-CEA or PBS in adjuvant; that is RIBI adjuvant was used for all immunizations.

Measurement of Anti-CEA Antibody Titers

C57BL/6 female mice were immunized as described above. Serum was collected seven days after the last immunization and assayed for the presence of anti-CEA antibodies by ELISA (enzyme linked immunosorbent assay). Briefly, the bV-CEA as well as bV-V and the nCEA were diluted in PBS at 1 $\mu$l of the mixture were incubated overnight at 37° C. in polyvinylchloride microtiter plates (Dinatech, Chantilly, Va.). Wells were treated with 5% bovine serum albumin (BSA) in PBS for 1 hr at 37° C. and sera at different dilutions were added. Following 1 hr incubation at 37° C., the plates were washed with 1% BSA in PBS. Peroxidase coupled goat anti-mouse (Gibco BRL) was added followed by incubation for 1 hr at 37° C. After washing, ophenylenediamine dihydrochloride was added in the presence of $H_2O_2$. After color development, the reaction was stopped with 50 $\mu$l of $H_2SO_4$ and the absorbance read at 490 nm. The titer of the sera was defined as the dilution factor required to reach an optical density (O.D.) of 1.2.

Lymphoproliferation Assay

C57BL/6 were immunized as described above to analyze induction of T cell activation by an assay measuring lymphocyte proliferation. One month following the last immunization, spleens were removed, mechanically dispersed through mesh screens and washed twice in serum free RPMI 1640 medium (Gibco, Gaithersburg, Md.). Erythrocytes and dead cells were removed by centrifugation over a Ficoll Hypaque gradient (density=1.119 g/ml) (Sigma Chemical Co., St. Louis, Mo.). Adherent cells were then depleted from the mononuclear population by incubation (30 min. at 37° C.) and passage over nylon wool columns (Robbins Scientific Corp., Sunnyvale, Calif.) resulting in a T cell enriched fraction. T lymphocytes were washed and resuspended in RPMI-1640 medium supplement with 15 mM HEPES (pH 7.4), 5% heat-inactivated fetal calf serum, 2 mM L-glutamine, 0.1 mM non-essential amino acids, 1 mM sodium pyruvate, 100 U/mL streptomycin (all from Gibco BRL, Gaithersburg, Md.) and $5\times10^{-5}$ $\beta$-mercaptoethanol (Sigma Chemical Co.).

T lymphocytes ($2\times10^5$/well) were incubated in the presence of irradiated, normal syngeneic splenocytes ($5\times10^5$/well) as antigen-presenting cells with and without various stimuli, such as concanavalin A (ConA) (Sigma, Chemical Co.), nCEA (Vitro Diagnostic), bV-CEA, or purified ovalbumin (Sigma Chemical Co.) Incubation was carried out in 96-well flat bottom plates (Costar Corp., Cambridge, Mass.) for up to 3 days (ConA) or 5 days (antigens). Cultures were pulsed with $^3$H-thymidine (1 $\mu$Ci/well) (Du Pont/NEN Research Products, Wilmington, Del.) for the final 18–24 hours of incubation. Cells were collected with a PhD cell harvester (Cambridge Technology, Cambridge, Mass.) and the incorporated radioactivity was measured by liquid scintillation spectroscopy (LS 3801 counter; Beckman Instruments, Duarte, Calif.)

Prevention of growth of CEA Transduced Tumors (MC-38-CEA-2)

Seven days following the last immunization, $2\times10^5$ MC-38-CEA-2 tumor cells were transplanted by subcutaneous injection. Animals were checked weekly for the presence of tumor. Tumors were measured by caliper in two dimensions and the volumes were calculated using the formula (width$^2\times$length)/2.

Results

Mice were first evaluated for the ability of nCEA to act as a boost in mice previously administered rV-CEA. As mentioned in Materials and Methods, RIBI adjuvant was used in all injections in this study in which nCEA, bV-CEA or control PBS were used as immunogen. When mice were administered one administration of rV-CEA followed by two boosts of PBS antibody titers to nCEA were modest, i.e., 1:250. Similar titer was seen when the immune sera were tested against bV-CEA. When mice received one injection of rV-CEA followed by two administrations of nCEA, antibody titers were at least 10 fold higher to both nCEA (1:3,450) as well as bV-CEA (1:4,500). Previous studies have shown that when mice were given three administrations of nCEA, antibody titers averaged 1:1,600 against nCEA and 1:2,950 against bV-CEA. Studies were then undertaken to determine if the immunization scheme of one immunization of rV-CEA followed by two immunizations of nCEA could enhance specific T cell responses to CEA. Results of these experiments are given in Table 1, as T cell proliferative responses to nCEA, bV-CEA, as well as to control antigen ovalbumin and ConA. These results are also given as "lymphocyte stimulation-induces" (LSI) in Table 2. The LSI is the $^3$H-thymidine incorporation of the test antigen divided by the $^3$H-thymidine incorporation of the control antigen ovalbumin. As can be seen in Tables 1 and 2, when mice were immunized three times with PBS, three times with nCEA, or one time with rV-CEA and two times with PBS, or one time with rV-CEA and two times with nCEA, the LSI values for ConA ranged from 110 to 240. When splenocytes of immunized mice were analyzed using 10 μg/ml of nCEA, however, the proliferation response to one immunization of rV-CEA plus two immunizations of PBS was 1.9 versus an LSI value of 26.6 when mice received rV-CEA plus two immunizations of nCEA. It should also be noted that when splenocytes of immunized mice were tested against 100 μg of nCEA the LSI of splenocytes of mice receiving three immunizations of nCEA was 39.6 versus 72.7 of mice receiving one injection of rV-CEA and two injections of nCEA. Similar results were seen when splenocytes of immunized mice were tested for proliferation responses using bV-CEA as an immunogen. These studies demonstrated that nCEA alone can elicit T cell responses to CEA and can also be used (perhaps more efficiently) in combination with rV-CEA to elicit specific anti-CEA T cell responses.

Studies were also carried out on the use of various immunization protocols to immunize mice against challenge with CEA expressing tumor cells. The transduction using a retroviral vector of the murine colon carcinoma cell line with CEA has been previously described. Robbins, P F, et al., *Cancer Res.* 1991;51:3657–62. In brief, these tumors express CEA and will grow in syngenic mice and kill transplanted animals. Horan Hand, P., et al., *Cancer Immunology Immunotherapy* 1993;36:65–75. As can be seen in Table 3, when mice received CEA transduced tumors following immunization with PBS, 7/9 mice had tumors at day 49 post transplant. When mice were given one administration of rV-CEA followed by two administrations of PBS, similar results were obtained, i.e., 7/10 mice had tumors. When mice were given either three administrations of nCEA, or one administration of rV-CEA followed by two administrations of nCEA, however, only 1/10 mice had tumors in both immunization groups.

Studies were then undertaken to determine if CEA derived from baculovirus could give similar results as those obtained with nCEA. Antibody titers of mice receiving one administration of rV-CEA followed by two administrations of bV-CEA averaged 1:14,800 against bV-CEA and were far in excess of the 1:250 average from mice receiving rV-CEA alone. Moreover, the induced antibodies were also shown to react with nCEA (1:8,600). As additional control in all these experiments, extracts of baculovirus devoid of the CEA gene (bV-V) were used and showed no reactivity. This control was employed to rule out the possibility that B cell responses were directed against baculovirus proteins as opposed to CEA specific responses. Previous studies have shown that when mice were given three administrations of bV-CEA, antibody titers averaged 1:3,100 against nCEA and 1:12,400 against bV-CEA. Bei, R., et al., *Mole Immunolo* 1994, 31:771–780.

As shown in Tables 4 and 5, lymphoproliferative responses and consequent LSIs were analyzed from splenocytes of mice receiving various immunization protocols of rV-CEA and/or bV-CEA. As shown in Tables 4 and 5, similar T cell proliferative responses were seen for all immunization groups to stimulation with ovalbumin or culture medium alone. Moreover, similar LSI results were seen in all immunization groups using ConA. As seen in Table 5, an LSI of 9.5 was seen using splenocytes of mice given three administrations of bV-CEA, after stimulation with 10 μg/ml of bV-CEA. However, when mice were given one administration of rV-CEA and then two administrations of bV-CEA, T cell proliferation responses of 36.7 were seen. A similar enhancement of T cell response when immunizing with rV-CEA plus bV-CEA as opposed to three administrations of bV-CEA were also seen when using nCEA for stimulation. Whereas, lymphocytes from mice administered bV-CEA three times elicited lower LSI after stimulation with nCEA as compared to those stimulated by bV-CEA. Similar humoral and T lymphoproliferative responses were obtained when the same adjuvant devoid of TDCM was used to immunize mice with bV-CEA after priming with rV-CEA (data not shown).

Studies were then undertaken to determine whether various immunization protocols employing bV-CEA could be used to protect mice against challenge with CEA transduced tumors. As can be seen in Table 6, at both day 35 and day 49 time intervals, the immunization protocol using a single injection of rV-CEA followed by two immunizations of bV-CEA were more efficient than the use of three immunizations of bV-CEA in terms of both numbers of mice with tumors and average tumor volume.

As shown in the studies described above, both bV-CEA and nCEA appear comparable in terms of inducing T cell responses and antibody responses either alone or in combination with rV-CEA. Moreover, both were able to protect mice against tumor challenge with CEA containing tumor cells when used in combination with rV-CEA. However, it should be pointed out that when bV-CEA was used alone as an immunogen the T cells proliferative response in vitro upon nCEA stimulation was lower as compared to those stimulated by bV-CEA and despite the high level of anti-nCEA antibodies. This result might be due to the differences of glycosylation between the two molecules.

TABLE 1

Lymphoproliferative responses of mice immunized with nCEA alone or nCEA after priming with recombinant vaccinia CEA.

| | Immunization Protocol | | | $^3$H Thymidine incorporation, cpm | | | |
|---|---|---|---|---|---|---|---|
| | | ConA | OVA | nCEA | | bV-CEA | |
| | Medium | 2 μg/ml | 100 μg/ml | 10 μg/ml | 100 μg/ml | 10 μg/ml | 50 μg/ml |
| PBS(3) | 1,213(±366)* | 161,321(±7,899) | 1,456(±159) | 1,846(±280) | 3,332(±2,252) | 3,196(±506) | 4,951(±506) |
| nCEA(3×) | 727(±235) | 139,980(±5,598) | 1,147(±107) | N.A[b] | 45,454(±2,015) | 11,990(±5,507) | 19,459(±5,507) |
| rV-CEA(1X) + PBS(2X) | 1,373(±442) | 204,449(±7,704) | 1,373(±451) | 2,654(±257) | 3,848(±736) | 11,510(±454) | N.A |
| rV-CEA(1X) + nCEA(2X) | 572(±264) | 253,760(±57.540) | 1,057(±594) | 28,161(±7,132) | 76,856(±3,814) | 36,960(±1,480) | N.A |

*Values = mean cpm ± standard deviation of triplicate wells.
[b]Not Available

TABLE 2

Lymphoproliferative responses of mice immunized with nCEA alone or nCEA after priming with recombinant vaccinia CEA.

| | LYMPHOCYTE STIMULATION INDEX (LSI)[a] | | | | | |
|---|---|---|---|---|---|---|
| | ConA | OVA | nCEA | | bV-CEA | |
| Immunization Protocol | 2 µg/ml | 100 µG/ML | 10 µg/ml | 100 µg/ml | 10 µg/ml | 50 µg/ml |
| PBS (3×) | 110 | 1 | 1.2 | 2.2 | 2.1 | 3.4 |
| nCEA (3×) | 122 | 1 | N.A[b] | 39.6 | 10.4 | 16.9 |
| rV-CEA (1×) + PBS (2×) | 148 | 1 | 1.9 | 2.8 | 8.4 | N.A |
| rV-CEA (1×) + nCEA (2×) | 240 | 1 | 26.6 | 72.7 | 34.9 | N.A |

[a]Proliferation in response to proteins is represented by an index of cpm in experimental wells divided by cpm of wells containing OVA 100 µg/ml.
[b]Not Available

TABLE 3

Effect of the immunization with nCEA alone or nCEA after priming with recombinant vaccinia CEA on the growth of MC-32-CEA-2 tumor cells that express human CEA.

| | Day 35 | | Day 49 | |
|---|---|---|---|---|
| Immunization Protocol | No. Mice with tumors/Total No. Mice | Average Volume (mm³) | No. Mice with tumors/Total No. Mice | Average Volume (mm³) |
| PBS (3×) | 8/10 | 575 | 7/9* | 1,990 |
| nCEA (3×) | 1/10 | 271 | 1/10 | 351 |
| rV-CEA (1×) + PBS (2×) | 7/10 | 690 | 7/10 | 3,574 |
| rV-CEA (1×) + nCEA (2×) | 1/10 | 974 | 1/10 | 7,096 |

" Mice were immunized as described in Materials and methods. PBS or nCEA were administered in adjuvant. Seven days following the last immunization, mice were injected with 2 × 10⁵ MC-38-CEA-2 tumor cells that express human CEA.
* 1 animal died

TABLE 4

Lymphoproliferative responses of mice immunized with bV-CEA alone or bV-CEA after priming with recombinant vaccinia CEA.

| Immunization Protocol | | | ³H Thymidine incorporation, cpm | | | | |
|---|---|---|---|---|---|---|---|
| | | ConA | OVA | nCEA | | bV-CEA | |
| | Medium | 2 µg/ml | 100 µg/ml | 10 µg/ml | 100 µg/ml | 10 µg/ml | 50 µg/ml |
| PBS(3X) | 1,213(±366)* | 161,321(±7,899) | 1,456(±159) | 1,846(±280) | 3,332(±2252) | 3,196(±506) | 4,951(±888) |
| bV-CEA(3×) | 657(±78) | 168,135(±11,975) | 1,686(±751) | N.A[b] | 6,724(±2,015) | 16.040(±3,576) | 25,187(±3.728) |
| rV-CEA(1X) + PBS(2X) | 1,373(±442) | 204,449(±7,704) | 1,373(±451) | 2,654(±257) | 3,848(±736) | 11,510(±454) | N.A |
| rV-CEA(1X) + bV-CEA(2X) | 1,141(±257) | 185,186(±18,753) | 1,846(±371) | 28,634(±5,467) | 31,634(±246) | 67,774(±9.079) | N.A |

*Values = mean cpm ± standard deviation of triplicate wells.
[b]Not Available

TABLE 5

Lymphoproliferative responses of mice immunized with nCEA alone or nCEA after priming with recombinant vaccinia CEA.

| | LYMPHOCYTE STIMULATION INDEX (LSI)[a] | | | | | |
|---|---|---|---|---|---|---|
| | ConA | OVA | nCEA | | bV-CEA | |
| Immunization Protocol | 2 µg/ml | 100 µG/ML | 10 µg/ml | 100 µg/ml | 10 µg/ml | 50 µg/ml |
| PBS (3×) | 110 | 1 | 2.2 | 2.2 | 2.2 | 3.4 |
| bVCEA (3×) | 99.7 | 1 | N.A[b] | 3.9 | 9.5 | 14.9 |

TABLE 5-continued

Lymphoproliferative responses of mice immunized with nCEA alone
or nCEA after priming with recombinant vaccinia CEA.

| | LYMPHOCYTE STIMULATION INDEX (LSI)[a] | | | | | |
|---|---|---|---|---|---|---|
| | ConA | OVA | nCEA | | bV-CEA | |
| Immunization Protocol | 2 µg/ml | 100 µG/ML | 10 µg/ml | 100 µg/ml | 10 µg/ml | 50 µg/ml |
| rV-CEA (1×) + PBS (2×) | 148 | 1 | 1.9 | 2.8 | 8.4 | N.A |
| rV-CEA (1×) + bVCEA (2×) | 100 | 1 | 15.5 | 16.8 | 36.7 | N.A |

[a]Proliferation in response to proteins is represented by an index of cpm in experimental wells divided by cpm of wells containing OVA 100 µg/ml.
[b]Not Available

TABLE 6

Effect of the immunization with nCEA alone or nCEA after priming with recombinant
vaccinia CEA on the growth of MC-32-CEA-2 tumor cells that express human CEA.

| | Day 35 | | Day 49 | |
|---|---|---|---|---|
| Immunization Protocol | No. Mice with tumors/Total No. Mice | Average Volume (mm³) | No. Mice with tumors/Total No. Mice | Average Volume (mm³) |
| PBS (3×) | 8/10 | 575 | 7/9* | 1,990 |
| bV-CEA (3×) | 5/9 | 179 | 6/8* | 972 |
| rV-CEA (1×) + PBS (2×) | 7/10 | 690 | 7/10 | 3,574 |
| rV-CEA (1×) + bV-CEA (2×) | 2/10 | 256 | 3/10 | 576 |

[a]Mice were immunized as described in Materials and methods. PBS or bV-CEA were administered in adjuvant. Seven days following the last immunization, mice were injected with 2 × 10⁵ MC-38-CEA-2 tumor cells that express human CEA.
*1 animal died

EXAMPLE 2

Generation of Human Cytotoxic T-cells Specific for
the Carcinoma Self-associated Antigen CEA Materials and Methods
Cell Cultures Colorectal carcinoma cell lines: SW403 (HLA-A2, A3), HT-29 (HLA-A1, A9), SW837 (HLA--, A19), SW1417 (HLA-A3,-) were purchased from American Type Culture Collection (Rockville, Md., USA). The cultures were mycoplasma free and were maintained in complete medium: DMEM (GIBCO, Grand Island, N.Y., USA) supplemented with 10% fetal bovine serum (FBS), 2 mM glutamine, 100 U/ml of penicillin, and 100 µg/ml of streptomycin (GIBCO). The T2 cell line (transport deletion mutant) (28) was a kind gift from Dr. Peter Cresswell (Yale University School of Medicine, New Haven, Conn., USA) and was maintained in Iscove's Modified Dulbecco medium (IMDM) containing 10% FBS.

EBV-transformed B cell lines designated as B-Vac24 and B-Vac01, and the B-Vac24 transfected with retroviral vector encoding a CEA construct designated as B-Vac24/CEA were maintained in RPMI1640 medium supplemented with 10% pooled human AB serum (Pel Freeze Clinical System, Brown Dear, Wis., USA), 2 mM glutamine, 100 U/ml of penicillin, and 100 µg/ml of streptomycin (GIBCO).

Peptide Synthesis

Peptide sequence of CEA was scanned for matches to the consensus motifs for HLA-A2 binding peptides. Nine, 10 and 11-mers peptides were selected for synthesis if they (a) fit the respective consensus motif and (b) diverged sufficiently from NCA and BGP so that an antigenic response might be anticipated. An NCA peptide that did not meet any known consensus motifs for human HLA-A2 was synthesized as a control. Syntheses were performed on an Applied Biosystem Model 432A personal peptide synthesizer and products were dissolved in aqueous solution, sterile-filtered and frozen at −70° at a concentration of 2 mg/ml. The purity of the peptides were >90% as analyzed by High Performance Liquid Chromatography (HPLC). The CEA peptides are listed in Table 7.

Peptide Binding Assay

Binding of CEA peptides to HLA-A2 molecule was analyzed by the upregulation of HLA-A2 expression of T2 cells as demonstrated by flow cytometry. T2 cell peptide binding assay has been reported recently. Nijman, H. W., et al. *Eur. J. Immunol.* 23:1215–1219, (1993). Briefly, aliquots of 0.5–1×10⁶ T2 cells in serum free IMDM were incubated with peptides at a concentration of 50 µg/ml in 24-well culture plates at 37° C. in 5% $CO_2$ overnight. T2 cells were washed and stained with an HLA-A2 specific antibody A2, 28 (#189 HA-1, One Lambda, Inc. Canoga Park, Calif., USA) using 10 µl of a 1×working dilution/10⁶ cells. MOPC-104E (Cappel/Organon Teknika Corp., West Chester, Pa.) was used as isotype control. The cells were then washed three times and incubated with a 1:100 dilution of phycoprobe PE anti-mouse IgM (Biomeda Corp., Foster City, Calif.). Analysis was carried out using the FACScan as above Cells were maintained on ice during all cell preparation and staining unless otherwise stated above.

Introduction of CEA Gene in EBV-Immortalized B-Cell Lines

B-cell lines were generated by a standard method Blumberg, R. S., et al., *J Infect Dis* 155: 877–880, (1987) using the B95-8 marmoset cell line supernatant containing EBV. Human pooled AB serum was used in all cell cultures in this study. EBV-immortalized B-cell lines were transduced with a retroviral expression construct of CEA.

Robbins, P. F., et al. *Cancer Res* 51: 3657–3662, (1991). Transduction was performed by co-cultivation of EBV-immortalized B cells with productively transduced amphotropic retroviral packaging cell lines PA317-CEA as described by Tsang et al. Tsang, K. Y., et al., *J Immunother* 13: 143–152, (1993). EBV immortalized B-cell transductants were selected in medium containing G418 at an active concentration of 0.7 mg/ml.

Generation of T Cell Line (TCL)

Peripheral blood mononuclear cells (PBMC) were obtained from heparinized blood from patients with metastatic carcinoma in a Phase I clinical trial employing recombinant vaccine in which the CEA gene was inserted into an attenuated vaccinia virus (rV-CEA). Kantor, J., et al *J Natl Cancer Inst* 84: 1084–1091, (1992); Kantor, J., et al. *Cancer Res* 52: 6917–6925, (1992). PMBC were obtained prior to and post administration of three injections of rV-CEA at monthly intervals at $10^5$ pfu (Vac 7), $10^6$ pfu (Vac 6), and $10^7$ pfu (Vac 24) per injection. PBMC from patients were separated using Lymphocyte Separation Medium gradient (Organon Teknika, Durham, N.C., USA) as previously described. Boyum, A., Cand *J. Clin. Lab Invest* 21:77–80 (1968). Washed PBMC were resuspended in complete medium: RPMI 1640 (GIBCO) supplemented with 10% pooled human AB serum (Pel-Freeze Clinical System, Brown Deer, Wis., USA), 2 mM glutamine, 100 U/ml penicillin and 100 $\mu$g/ml of streotomycin (GIBCO). $2\times10^5$ cells in complete medium in a volume of 100 $\mu$l were added into each well of 96-well flat-bottom assay plate (Costar, Cambridge, Mass., USA). Peptides were added to cultures at a final concentration of 50 $\mu$g/ml. Cultures were incubated for 5 days at 37° C. in a humidified atmosphere containing 5% $CO_2$. After removal of the peptide containing medium, the cultures were then provided with human IL-2 (10 U/ml) for 11 days, with IL-2 containing medium being replenished every 3 days. The 5 day peptide plus 11 day IL-2 incubations constitute one cycle. Primary cultures were restimulated with the same peptide (50 $\mu$g/ml on day 16 to begin the next cycle. $5\times10^5$ irradiated (4,000 rad) autologous PBMC were added in a volume of 50 $\mu$l in complete medium as antigen-presenting cells (APC).

Cytotoxicity Assays

Various target cells were labeled with 50 $\mu$Ci of 111-Indium ($^{111}$In) oxine (Medi-Physics Inc., Arlington, Ill., USA) for 15 min. Target cells ($0.5\times10^4$) in 100 $\mu$l were added to each of 96 wells in U-bottom assay plates (Costar). The labeled targets were incubated with peptides at a final concentration of 50 $\mu$g/ml for 60 min at 37° C. in $CO_2$ before adding effector cells. Effector cells were suspended in 100 $\mu$l of complete medium supplemented with 10% pooled human AB serum and added to target cells, and the plates were then incubated at 37° C. in 5% $CO_2$ for 12 to 18 hr. Supernatant was harvested for gamma counting with use of Skatron Harvestor frames (Sterling, Va., USA). Experiments were carried out in triplicate. Specific lysis was calculated with the use of the following formula:

$$\text{Lysis \%} = \frac{\text{observed release (cpm)} - \text{spontaneous release (cpm)} \times 100}{\text{total release (cpm)} - \text{spontaneous release (cpm)}}$$

Spontaneous release was determined from wells to which 100, $\mu$l of complete medium were added. Total releasable radioactivity was obtained after treatment of targets with 2.5% Triton X-100.

Detection of Cytokine

Supernatants of T cells exposed for 3 days to peptides and APC in IL-2 free medium at a responder to stimulator ratio of 4:1 ($4\times10^6$: $10^6$ cells/ml) were screened for the secretion of TNF-$\alpha$ using enzyme-linked-immunosorbent assay kit (Genzyme, Cambridge, Mass., USA). The results were expressed in pg/ml.

Flow Cytometry

The procedure for single color flow cytometric analysis has been previously published. Guadagni et al., *Cancer Res.* 50:6248–6254 (1990). Briefly, $1\times10^6$ cells were washed three times with cold $Ca^{2+}$-free Dulbecco's PBS (DPBS) and then stained for 1 hr with 1 $\mu$g of MAb against CD3 (Beckton Dickinson, San Jose, Calif.), CD4 (Becton Dickson), CD8 (Becton Dickinson), HLA class 1 (W6/32) (Sera-Lab, Sussex, England), HLA class II (DR) (Beckton Dickinson), and MOPC-21 (Cappel/Organon Teknika Corp., West Chester, Pa.) in a volume of 100 $\mu$l of PBS containing 1% bovine serum albumin. Anti-CEA MAb COL-1 was used as 100 $\mu$l of culture supernatant. The cells were then washed three times with cold DPBS and incubated for an additional hr in the presence of 1:100 dilution (volume of 100 $\mu$l of PBS containing 1% bovine serum albumin) of fluorescein-conjugated goat anti-mouse lg (Kirkegaard and Perry Laboratory, Gaithersburg, Md.). The cells were again washed three times with DPBS and resuspended in DPBS at a concentration of $1\times10^6$ cells/ml. The cells were immediately analyzed using a Beckton Dickinson FACScan equipped with a blue laser with an excitation of 15 nW at 488 nm. Data were gathered from 10,000 cells using a live gate, stored, and used to generate results.

The procedure for dual color flow cytometric analysis was similar to that for single color analysis with the following exceptions. The antibodies used were anti-CD4 fluorescein conjugate, anti-CD8 phycoerythrin conjugate, anti-lgG$_1$ fluorescein conjugate, and anti-lgG$_{2a}$ phycoerythrin conjugate (Becton Dickinson). Staining was done simultaneously for 1 hr after which cells were washed three times, resuspended as above, and immediately analyzed using a Becton Dickinson FACSort equipped with a blue laser with an excitation of 15 nW at 488 nm equipment with Lysis™II program.

HLA Typing

The HLA phenotyping of patients was kindly performed by the Tissue Typing QC Laboratory, Naval Medical Research Institute using a standard antibody-dependent microcytotoxicity assay and a defined panel of anti-HLA antisera. The HLA phenotypes were as follows: Patient Vac24 [HLA-A2,24 (9); B44 (12,w4), 51 (5,W4); DR 4,11 (5); DQ 3,7 3); DR w52,53]; Patient Vac01 [HLA-A28,31; B14,35; DR1, 4; DQ1,3; Drw53]; Patient Vac23 [HLA-A1, 26 (10); B8 (w6), 60 (40,w6); CW3,7; DR0103, 15 (2); DQ5 (1),6(1)]; Patient Vac32 [HLA-A3, 68(28); B7 (w6), 51 (5,w4); CW7; DR4, 15(2); DQ1,8(3); DRw53]; patient Vac6[HLA-A2,24(9); B13(W4); CW6; DR7, 8; DQ4; DR53], an patient Vac7 [HLA-A2; B7(W6); CW7: DR15(2), 17(3); DQ1,2; DR52].

Vaccinia Virus Infection of Colorectal Carcinoma Cells cDNA for HLA-A2.1 gene and human $\beta$2-microglobulin gene in vaccinia virus vector were obtained from Dr. D. Cole (Surgery Branch, NCI, NIH). These genes were inserted into the TK gene in plasmid pSCII, allowing homologous recombination to occur with the viral TK gene. O'Neil, B. H., et al. *J Immunol* 151: 1410–1418, (1993). Target cells at a concentration of $1\times10^7$/ml in complete RPMI1640 medium supplemented with 0.1% BSA were incubated with an equal volume of vaccinia virus ($10^8$ plaque-forming unit/ml) in the same medium at 37° C. for 1.5 hr. The cells were then adjusted to a concentration of $5\times10^5$/ml in complete medium and incubated for 3 hr at 37° C. Coinfection of vaccinia- HLA-A2 and vaccinia-β2-microglobulin was done at a multiplicity of infection of 10:1.

Statistical Analysis

Statistical analysis of differences between means was done by a paired T-test.

Results

Since the entire amino acid sequence of human CEA is known and human HLA class I A2 consensus motifs have been described [Falk, K., et al., *Nature* 351: 290–296 (1991); Hunt, D. F., et al., *Science* 255: 1261–1263, (1992)], studies were undertaken to identify a series of peptides that would potentially bind class I A2 molecules. A2 was chosen since it is the most common HLA class I molecule, being represented in approximately 50% or North American caucasians and 34% of African Americans. Lee J., Springer-Verlag, New York 6: 154, (1990). The peptide sequence of CEA was thus examined for matches to the consensus motifs for HLA-A2 binding peptides. Peptides were only selected, moreover, if their sequence diverged sufficiently from the CEA-related NCA and BGP sequences. The amino acid sequence of human CEA (GeneBank Accession #M17303) was scanned using a predictive algorithm [Parker, K. C., et al., *J Immunol* 152: 163–175, (1994)] that combines a search for anchor residues with numerical assignments to all residues at all positions. Ten peptides were synthesized using this algorithm, ranging in length from 9 to 11 amino acids. Six of these peptides also contained the HLA-A2 motif of leucine or isoleucine at position 2 and valine or leucine at the C terminal. Another peptide (CAP-7) also possessed the motif for binding to HLA-A3. DiBrino, M., et al., *Proc Natl Acad Sci* 90: 1508–1512, (1993). All peptides were selected to have minimal homology to the parallel regions of NCA and BGP, after optimal alignment of the latter sequences with CEA. The 9 mer, 10 mer or 11 mer peptides that met these criteria were selected for synthesis and purificiation; they were designated CAP (Carcinoembryonic Antigen Peptide)-1 through 10 (SEQ ID NOS: 1–10). Their amino acid sequence and position in the CEA molecule are given in Table 7. The positive (P) or negative (N) designation (Table 7) relates to the predicted binding to HLA-A2.

The T2 cell binding assay has been used to predict human HLA-A2 consensus motifs. Nijman, H. W., et al., *Eur. J. Immunol.* 23:1215–1219 (1993). In this assay, the binding of an appropriate peptide results in the upregulation of surface HLA-A2 on the T2 cells, which can be quantified via FACScan using an anti HLA-A2 antibody. As seen in Table 7, seven of the CEA peptides (CAP-1 through CAP-7) scored positive for T2 binding (the peptides were designated CAP-1 through 10 retrospectively on the basis of their quantitive binding to T2). Since peptide 571–579 (designated CAP-1) demonstrated the highest level of T2 binding, the peptide reflecting the NCA analog (the corresponding NCA peptide obtained after optimal alignment of NCA and CEA), was also synthesized and tested; this peptide, designated NCA-1, showed background binding to T2 (Table 7). This was consistent with the fact that an amino acid substitution in NCA had abolished one of the A2 anchor residues (Arg for Leu at position 2).

In an attempt to establish T-cell lines from patients who had received the rV-CEA construct, PBLs were obtained from three patients (designated Vac6, Vac7, and Vac24) who express the HLA-A2 allele and alternately pulsed with 50 μg/ml peptide CAP-1 and IL-2 (10 U/ml) as described in the Methods section. In all three cases T-cell lines could be established which were cytotoxic for T2 cells when pulsed with CAP-1 peptide. FIG. 1 shows the results of these assays using T-cell lines from patients V24 and V6. The T-cell line from patient Vac24 was chosen for further study.

PBLs from patient Vac24 (pre-and post-vaccination with 3 doses of $10^7$ pfu rv-CEA at monthly intervals) were placed in 96 well plates and pulsed with the CAP-1 peptide and then IL-2 as described in the Methods section. Each exposure to peptide and IL-2 was considered one cycle of stimulation. As seen in Table 8, one, two, or three cycles of CAP-1 peptide and IL-2 did not result in growth of cells in any of the 96 wells using the pre-immunization PBLs. By contrast after one cycle of stimulation of post-vaccination PBLs from the same patient, 66 of the 96 wells (68%) demonstrated growth of cells, which were maintained through four cycles of stimulation. It is of interest, that after four cycles of stimulation of pre-immunization PBSs, 2/96 wells (2%) exhibited cell growth. Thus, one could hypothesize that a minor population of T-cells exist in this patient capable of recognizing a specific CEA epitope (571–579), and that these cells were clonally expanded as a result of the rV-CEA administration.

Sufficient PBSs pre-and post-vaccination with rV-CEA at the $10^7$ pfu dose, were also available from two non-HLA-A2 patients: Vac32(HLA A1,26) and Vac23 (HLA A3,68). Since we had little or no basis for predicting which peptides might bind to these haplotypes, nine of the CEA peptides were used in an attempt to establish T-cell lines. Using peptide CAP-1 with IL-2 as described above, no T-cell lines could be established from pre-immunization PBLs from either patient Vac32 or Vac23 (Table 9). However, employing post-rV-CEA immunization PBLs, T-cell lines were established after 3 cycles of stimulation in 25/48 wells (52%) for patient Vac32 and in 21/48 wells (43%) for patient Vac23 (Table 9).

A similar contrast in pre-versus post-vaccination PBLs from patients Vac32 and Vac23 was seen with a mixture of CEA peptides CAP-4, 6 and 7 (Table 9). Combinations were used as an initital screen to conserve PBLs. It is perhaps of significance that PBL from Vac32 (HLA-A3 positive) showed evidence of cell growth in the presence of CAP-7, the peptide that bears the HLA-A3 binding motif. It should be noted that these results suggest that a peptide shown to bind to HLA-A2 can also stimulate T-cell lines after binding to some non-A2 antigens; the possible reasons for this will be discussed in detail below. However, it was decided to first characterize the T-cell responses in patient Vac24 because of the implied relevance of MHC binding and T-cell activation. Nonetheless, it is encouraging that PBL from 5/5 patient showed signs of T-cell response to peptide CAP-1 post immunization with rV-CEA.

Flow cytometric studies were conducted to phenotype the V24T, V6T and V7T-cell lines. The results are shown in Table 10. Cells stained double positive for both CD8 and CD4 and V24T and V6T cell lines, while the V7T cell line was $CD8^+$.

To determine if the Vac24 T-cell line (designated V24T) could lyse autologous B-cells presenting the CAP-1 peptide, B-cells from patient Vac24 were first transformed with EBV and then pulsed (i.e., incubated) with the CAP-1 peptide. As seen in Table 11, the V24T-cells were capable of lysing the autologous B-cells when pulsed with CAP-1, but when an allogeneic (non-HLA-A2) EBV-transformed B-cell was pulsed with the same peptide, no lysis was observed. When the NCA-1 peptide, reflecting the analogous region on the NCA molecule was used to pulse Vac24 B-cells; no lysis was observed with the V24T-cells. As shown in Table 7, this was not unexpected since 3 of the 9 amino acids of NCA-1 differ from those of CAP-1, including an anchor residue.

Studies were undertaken to determine if the CAP-1 peptide could induce the secretion of TNF-α from the cytolytic V24T-cells. As shown in FIG. 2, incubation of V24T-cells with autologous B-cells pulsed with CAP-1 peptide resulted in the production of substantial TNF-α, while control peptides CAP-9 and CAP-10 failed to show this effect.

While the above results indicate that autologous B-cells present the CAP-1 peptide to the Vac24 cells, resulting in lysis of the B-cells, they do not indicate that human APCs can endogenously process the entire CEA molecule in a manner so as to bind HLA-A2 molecules for presentation at the cell surface. To help answer this question, EBV transformed B-cells of patient Vac24 were transduced with the entire human CEA gene using a retroviral vector (see Methods). As seen in Table 12, the CEA-transduced cells now express CEA, and the transduction process had no effect on expression of (cells bearing) HLA class I and class II molecules.

As shown in Table 13, the autologous B-cells transduced with the CEA gene can now serve as targets for the V24 CTLs. These results thus demonstrate that a CEA gene product can be endogenously processed by autologous B-cells and presented at the cell surface in the context with class I MHC to induce T-cell lysis. The question now remained as to whether human carcinoma cells can act in the same manner as APCs and thus serve as potential targets for V24T-cells. As seen in Table 13, non-A2 allogenic carcinoma cells SW1417 and HT-29, which do express substantial CEA cannot serve as targets while the allogeneic A2 positive SW403 carcinoma cells expressing CEA are lysed.

To further demonstrate the HLA-A2 restricted nature of the V24T-cells in the lysis of human carcinoma cells, the CEA positive, non-A2 SW837 human carcinoma cell line was employed. These cells were either uninfected, infected with wild type vaccinia virus, or infected with recombinant vaccinia virus containing the HLA-A2 gene. As seen in Table 14, only the carcinoma cells infected with rV-A2.1 recombinant expressed A2, and only these cells were susceptible to lysis with V24T cells. These studies further demonstrate the HLA-A2 restricted nature of the CEA specific lysis of the V24T-cells.

TABLE 7

Binding of CEA peptides to HLA-A2 molecule

| Peptide | Position | Sequence | Predicted Binding The HLA Class 1A2[a] | T2 binding Assay[b] Exp 1 | Exp2 |
|---|---|---|---|---|---|
| CAP-1 | 571–579 | YLSGANLNL (SEQ ID NO: 1) | P | 561 | 806 |
| CAP-2 | 555–564 | VLYGPDTPII (SEQ ID NO: 2) | P | 515 | 796 |
| CAP-3 | 87–96 | TLHVIKSDLV (SEQ ID NO: 3) | P | 480 | ND |
| CAP-4 | 1–11 | KLTIESTPFNV (SEQ ID NO: 4) | P | 441 | ND |
| CAP-5 | 345–354 | TLLSVTRNDV (SEQ ID NO: 5) | P | 405 | ND |
| CAP-6 | 19–28 | LLVHNLPQHL (SEQ ID NO: 6) | P | 381 | ND |
| CAP-7 | 27–35 | HLFGYSWYK (SEQ ID NO: 7) | N | 326 | ND |
| CAP-8 | 523–532 | TLFNVTRNDA (SEQ ID NO: 8) | N | 260 | ND |
| CAP-9 | 137–146 | TQDATYLWWV (SEQ ID NO: 9) | N | 204 | ND |
| CAP-10 | 102–110 | GQFRVYPEL (SEQ ID NO: 10) | N | 201 | ND |
| NCA-1 | 571–579 | YRPGENLNL (SEQ ID NO: 11) | N | 252 | 225 |
| Positive Control | — | ALAAAAAAV (SEQ ID NO: 12) | P | 632 | — |
| No Peptide | — | — | — | 280 | 300 |

[a]Predicted binding on the basis of published motifs. Folk, et al., Nature 351: 290–296 (1991).
[b]Reactivity of T2 cells with anti-HLA-A2 Mab after the cells were incubated with CEA peptide. Peptides were used in concentration of 50 μg/ml/ $10^6$ cells. The results are expressed in relative fluorescence values. Positive control 9-mer is an A2 binding motif.

TABLE 8

Frequency of T Cell Growth from Patient Vac24 Following an In Vitro Stimulation with CAP-1 Peptide: Pre- and Post Immunization with rV-CEA

| | Stimulation cycle | | | |
|---|---|---|---|---|
| Pre or Post Immunization | 1[a] | 2 | 3 | 4 |
| Pre | 0[b] | 0 | 0 | 2 |
| Post | 66 | 66 | 66 | 66 |

[a]cycle of stimulation. See Material and Methods for details with CEA-CAP-1, 9 mer peptide an IL-2.
[b]Results were expressed as the number of positive wells/96 wells. PBMC were seeded at a concentration of $1 \times 10^5$ cell/200 μl/well.

TABLE 9

Frequency of T Cell Growth Following an In Vitro Stimulation with CEA Peptides: Pre and Post Immunization with rV-CEA

| | | Frequency | | | | | |
|---|---|---|---|---|---|---|---|
| | | Pre | | | Post | | |
| Patient | Peptide | 1[a] | 2 | 3 | 1 | 2 | 3 |
| VAC32 | CAP-4, CAP-6, CAP-7 | 0[b] | 0 | 4 | 0 | 0 | 30 |
| | CAP-3, CAP-10, CAP-9 | 0 | 0 | 0 | 0 | 0 | 0 |
| | CAP-8, CAP-2 | 0 | 0 | 0 | 0 | 0 | 0 |
| | CAP-1 | 0 | 0 | 0 | 0 | 0 | 25 |
| VAC23 | CAP-4, CAP-6, CAP-7 | 0 | 0 | 3 | 0 | 0 | 31 |
| | CAP-3, CAP-10, CAP-9 | 0 | 0 | 0 | 0 | 0 | 0 |
| | CAP-8, CAP-2 | 0 | 0 | 0 | 0 | 0 | 0 |
| | CAP-1 | 0 | 0 | 0 | 0 | 0 | 21 |

[a]cycle of stimulation with peptide IL-2 (see Material and Methods).
[b]Results were expressed as the number of positive wells/48 wells. PBMC were seeded at a concentration of $1 \times 10^6$ cells/well in 1 ml.

TABLE 10

FLOW CYTOMETRIC ANALYSIS OF SURFACE MARKERS ON T-CELL LINES

| Surface antigen | V24T | V6T | V7T |
|---|---|---|---|
| CD8/CD4 | 62.4 | 30.8 | Negative |
| CD8 | 35.7 | 56.0 | 99.6 |
| CD4 | Negative | 12.6 | Negative |
| CD3 | 98.5 | 95.4 | 99.4 |

Negative, <5% positive. Results are expressed in percentage of each T-cell line reactive with MAbs. Routinely 2–4% of the cells were stained when treated with either with no primary MAb or an isotype-matched control MAb.

TABLE 11

Ability of V24T-cells (T-cells derived from PBLs from rV-CEA Vaccinated Patient) to Lyse Autologous and Allogenic B-Cells Pulsed with a CEA Specific Peptide

| B-Cells | HLA-A2 | Pulsing Peptide | % Lysis |
|---|---|---|---|
| B-V24 | + | CAP-1 | 43% (0.29) |
| | | NCA-1 | 8% (1.92) |
| | | none | 2% (0.37) |
| B-V01 | − | CAP-1 | 10% (0.53) |
| | | NCA-1 | 11% (0.62) |
| | | none | 8% (0.68) |

A 18hr[111] In release assay was performed. Peptides were used in a concentration of 50 μg/ml. Results are expressed as percentage specific lysis at E/T raios of 25:1.
Number in parenthisis is standard deviation.
Bold number, statistically significant (p < 0.01) (paired t-test).

TABLE 12

Flow Cytometric Analysis of Surface Antigens of EBV Transformed B-cells derived from Patient Vac24 (designated B-Vac24): Before and After Transfection with CEA

| | | % Positive | |
|---|---|---|---|
| Antigen | MAb | B-VAC24[a] | B-Vac24 (CEA)[b] |
| CEA | COL-1 | 4.4 (24.7)[c] | 42.9 (100.9) |
| HLA class I | W6/32 | 100.0 (831.9) | 100.0 (519.1) |
| HLA class II | anti-HLA-DR | 99.8 (313.3) | 99.3 (221.8) |
| Control | MOPC-21 | 2.2 (30.5) | 2.0 (24.1) |

[a]B-Vac24 are EBV transformed B-cells derived from PBL of patient Vac 24 prior to immunization with rV-CEA.
[b]B-Vac24 (CEA) are the same as B-Vac24 except they have been transduced with the entire human CEA gene using a retroviral vector as described in Materials and Methods.
[c]Values represent the percentage of each cell type reactive with MAbs listed as analyzed by flow cytometry. Numbers in paranthesis are the mean channel fluorescence intensity as determined in relative log units. Routinely 2–4% of the cells were stained when treated either with no primary MAb or an isotype-matched control MAb. LS174T, a colorectal carcinoma cell line, was used as a positive for CEA expression. The % positive value for CEA in CEA expressing LS174T human colon carcioma cell line was 59.8 (144.4).

TABLE 13

Cytotoxicity of V24T-Cell Line (derived from a patient immunized with rV-CEA) on Target Cells with Endogenous CEA Expression

| Target | HLA-A2 | CEA | % Lysis |
|---|---|---|---|
| B-VAC24[a] | + | − | 8.2 (2.1) |
| B-VAC24 (CEA)[a] | + | + | 46.1 (11.6) |
| SW403[b] | + | + | 45.2 (1.5) |
| SW1417[b] | − | + | 5.2 (0.5) |
| HT-29[b] | − | + | 4.1 (0.6) |

[a]As described in the legend to Table 11.
[b]Human colon carcinoma cell lines expressing CEA.
HLA-A2 and CEA expression were tested by blow cytometry using MAbs anti-A2 and COL-1 respectively. A 18 hr[111] In release assay was performed. Results are expression in % specific lysis at E:T ratio = 50:1. The number in parentheses is the standard derivation. Bold numbers, statistically significant lysis (p < 0.01) (paired t-test).

TABLE 14

Demonstration of HLA-A2 involvement in Ability of V24T Cells to Lyse Human Colon Carcinoma Cells

| | Expression of MHC class 1 molecules[a] | | |
|---|---|---|---|
| Infection | W6/32 | A2.28 | % Lysis[b] |
| None | 99.1 (228.23) | 4.4 (47.41) | 8.2 (1.4) |
| Vaccinia A2.1 | 99.3 (261.75) | 90.4 (66.70) | 31.4 (2.5) |
| Vaccinia vector control | 99.4 (217.59) | 2.9 (17.54) | 7.2 (0.6) |

SW837, an HLA-A2 negative and CEA positive, human colorectal carcinoma cell line was infected with vaccinia A2.1. The surface expression of HLA-A2 molecule after infection was analyzed by flow cytometry using anti-HLA-A2 MAb and W6/32 antibody.
[a]Values represent the percentage of cells reactive with the antibodies listed. Number in parentheses are the mean fluorescence intensity as determined in relative log units.
[b]Results are expressed in % specific lysis in a 12-hr[111] In release assay at E:T ratio = 50:1. The number in parentheses is the standard derivation. Bold numbers, statistically significant lysis (p < 0.01) (paired t-test).

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A method for generating human cytotoxic T-cells specific for a human carcinoembryonic antigen comprising:

(a) introducing a sufficient amount of a first pox virus vector to a host to stimulate production of cytotoxic T cells, wherein said first pox virus vector contains a DNA segment encoding a human carcinoembryonic antigen (CEA) operably linked to a promoter capable of expression in the host; and (b) at least one periodic interval thereafter introducing into the host additional antigen by a second pox virus vector of the genus different from said first pox virus vector wherein said vector contains the DNA segment encoding the human CEA or encoding a peptide comprising at least one of SEQ ID NOS: 1–7, or by adding to the host a human CEA or a peptide selected from the group consisting of SEQ ID NOS: 1–7.

2. The method of claim 1, wherein the first pox virus is selected from the group of pox viruses consisting of suipox, avipox, capripox and orthopox virus.

3. The method of claim 2, wherein the orthopox virus is vaccinia.

4. The method of claim 2, wherein the avipox is fowlpox, canary pox or pigeon pox.

5. The method of claim 2, wherein the suipox is swinepox.

6. The method of claim 1, wherein the first pox virus vector is vaccinia and the second pox virus vector is selected from the group of pox viruses consisting of suipox, avipox, capripox and orthopox virus.

7. The method of claim 1, wherein the additional antigen is formulated with an adjuvant or is in a liposomal formulation.

8. The method of claim 7, wherein the adjuvant is selected from the group consisting of RIBI Detox, QS21 and incomplete Freund's adjuvant.

9. A method for generating human cytotoxic T-cells specific for a human carcinoembryonic antigen (CEA) comprising:

(a) introducing a sufficient amount of a first pox virus vector to a host to stimulate production of cytotoxic T cells, wherein said first pox virus vector contains a DNA segment encoding a peptide comprising SEQ ID NO:1 operably linked to a promoter capable of expression in the host; and (b) at least one periodic interval thereafter introducing into the host additional antigen by a second pox virus vector of the genus different from said first pox virus vector wherein said vector comprises a DNA segment encoding a human CEA or encoding a peptide comprising at least one of SEQ ID NOS: 1–7, or by adding to the host a human CEA or a peptide selected from the group consisting of SEQ ID NOS: 1–7.

10. The method of claim 9, wherein the first pox virus is selected from the group of pox viruses consisting of suipox, avipox, capripox and orthopox virus.

11. The method of claim 10, wherein the orthopox virus is vaccinia.

12. The method of claim 10, wherein the avipox is fowlpox, canary pox or pigeon pox.

13. The method of claim 10, wherein the suipox is swinepox.

14. The method of claim 1, wherein the first pox virus vector is vaccinia and the second pox virus vector is selected from the group of pox viruses consisting of suipox, avipox, capripox and orthopox virus.

15. The method of claim 1, wherein the additional antigen is formulated with an adjuvant or is in a liposomal formulation.

16. The method of claim 15, wherein the adjuvant is selected from the group consisting of RIBI Detox, QS21 and incomplete Freund's adjuvant.

\* \* \* \* \*